US00PP34447P2

(12) United States Plant Patent
Kobayashi

(10) Patent No.: US PP34,447 P2
(45) Date of Patent: Jul. 26, 2022

(54) **NEW GUINEA *IMPATIENS* PLANT NAMED 'DONGIPETRESTA 21'**

(50) Latin Name: *Impatiens hawkeri*
Varietal Denomination: 'Dongipetresta 21'

(71) Applicant: DUMMEN GROUP B.V., De Lier (NL)

(72) Inventor: Ruth Kobayashi, Carlsbad, CA (US)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/571,203

(22) Filed: Jan. 7, 2022

(51) Int. Cl.
*A01H 5/02* (2018.01)
*A01H 6/16* (2018.01)

(52) U.S. Cl.
USPC ..... Plt./318.1
CPC ..... *A01H 6/165* (2018.05)

(58) Field of Classification Search
USPC ..... Plt./318.1
CPC ..... A01H 6/165
See application file for complete search history.

*Primary Examiner* — Anne Marie Grunberg
(74) *Attorney, Agent, or Firm* — C. Anne Whealy

(57) ABSTRACT

A new and distinct cultivar of *Impatiens* plant named 'Dongipetresta 21' characterized by its upright to outwardly spreading and mounding plant habit; moderately vigorous to vigorous growth habit; freely branching habit; dark green-colored leaves; freely and early flowering habit; medium-sized red and light reddish pink bi-colored flowers; and good garden performance.

2 Drawing Sheets

Figure 1:
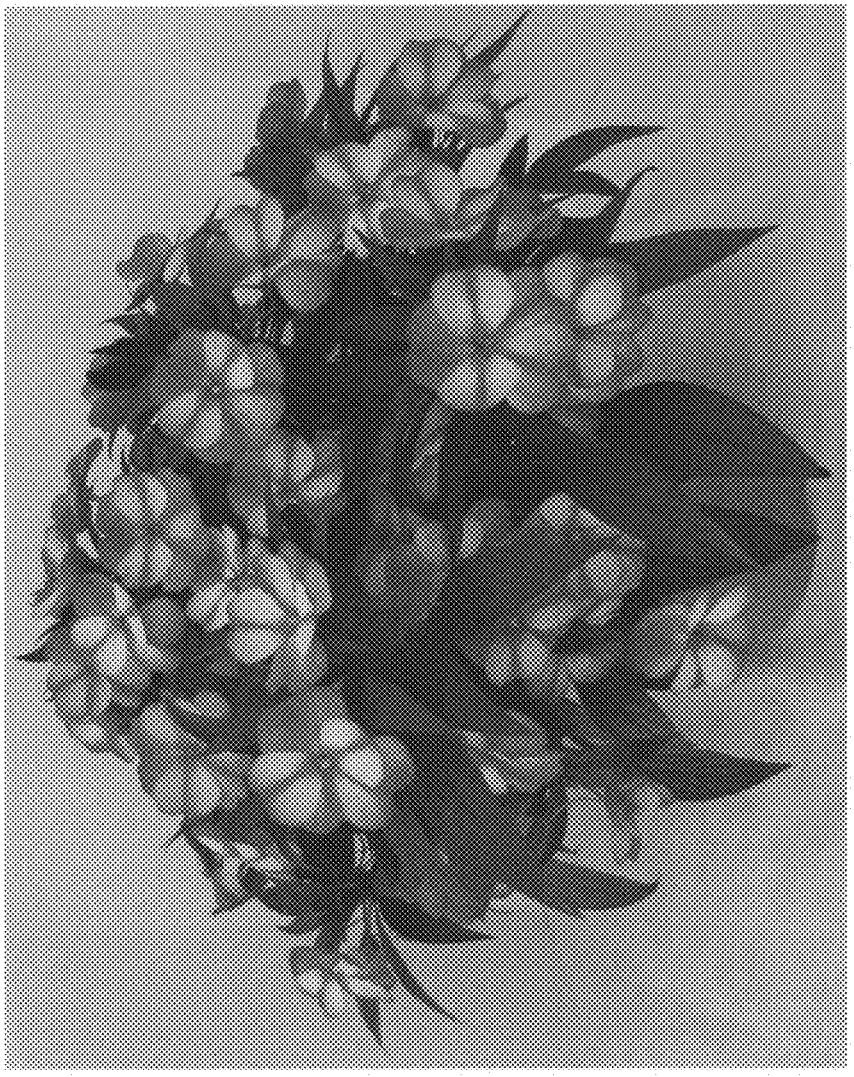

Botanical designation: *Impatiens hawkeri.*
Cultivar denomination: 'DONGIPETRESTA 21'.

STATEMENT REGARDING PRIOR DISCLOSURES BY INVENTOR & APPLICANT/ASSIGNEE

The Inventor and Applicant assert that no publications nor advertisements relating to sales, offers for sale or public distribution occurred more than one year prior to the effective filing date of this application. Any information about the claimed plant would have been obtained from a direct or indirect disclosure from the Inventor and/or Applicant. Inventor and Applicant claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of New Guinea Impatiens plant, botanically known as *Impatiens hawkeri* and hereinafter referred to by the name 'Dongipetresta 21'.

The new *Impatiens* plant is a product of a planned breeding program conducted by the Inventor in Koka, Ethiopia and Encinitas, Calif. The objective of the breeding program is to create new freely-branching, early and freely flowering New Guinea Impatiens plants with large attractive flowers and good garden performance.

The new *Impatiens* plant originated from a cross-pollination made by the Inventor in November, 2017 in Koka, Ethiopia of *Impatiens hawkeri* 'Kiamuna', disclosed in U.S. Plant Pat. No. 20,983, as the female, or seed, parent with a proprietary selection of *Impatiens hawkeri* identified as code number NN12-003632-006, not patented, as the male, or pollen, parent. The new *Impatiens* plant was discovered and selected by the Inventor as a single flowering plant from within the progeny of the stated cross-pollination in a controlled greenhouse environment in Encinitas, Calif. in April, 2018.

Asexual reproduction of the new *Impatiens* plant by terminal vegetative cuttings in a controlled greenhouse environment in Encinitas, Calif. since June, 2018 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongipetresta 21'. These characteristics in combination distinguish 'Dongipetresta 21' as a new and distinct *Impatiens* plant:

1. Upright to outwardly spreading and mounding plant habit.
2. Moderately vigorous to vigorous growth habit.
3. Freely branching habit.
4. Dark green-colored leaves.
5. Freely and early flowering habit.
6. Medium-sized red and light reddish pink bi-colored flowers.
7. Good garden performance.

Plants of the new *Impatiens* can be compared to plants of the female parent, 'Kiamuna'. Plants of the new *Impatiens* differ primarily from plants of 'Kiamuna' in flower color as flowers of plants of the new *Impatiens* are red and light reddish pink bi-colored whereas flowers of plants of 'Kiamuna' are red and light red purple bi-colored.

Plants of the new *Impatiens* can be compared to plants of the male parent selection. Plants of the new *Impatiens* differ primarily from plants of the male parent selection in the following characteristics:

1. Plants of the new *Impatiens* are not as vigorous as plants of the male parent selection.
2. Plants of the new *Impatiens* flower earlier than plants of the male parent selection.
3. Flowers of plants of the new *Impatiens* are red and light reddish pink bi-colored whereas flowers of plants of the male parent selection are bright red and light pink bi-colored.

Plants of the new *Impatiens* can be compared to plants of *Impatiens hawkeri* 'Duepetrest', disclosed in U.S. Plant Pat. No. 11,375. In side-by-side comparisons, plants of the new *Impatiens* differ primarily from plants of 'Duepetrest' in the following characteristics:

1. Plants of the new *Impatiens* are more vigorous than plants of 'Duepetrest'.
2. Plants of the new *Impatiens* have larger flowers than plants of 'Duepetrest'.
3. Flowers of plants of the new *Impatiens* are red and light reddish pink bi-colored whereas flowers of plants of 'Duepetrest' are soft red and light lavender bi-colored.

Plants of the new *Impatiens* can also be compared to plants of *Impatiens hawkeri* 'Tamar Purple Bicolor', disclosed in U.S. Plant Pat. No. 15,462. In side-by-side comparisons, plants of the new *Impatiens* differ primarily from plants of 'Tamar Purple Bicolor' in the following characteristics:

1. Plants of the new *Impatiens* flower about one week earlier than plants of 'Tamar Purple Bicolor'.
2. Plants of the new *Impatiens* flower have slightly smaller flowers than plants of 'Tamar Purple Bicolor'.
3. Flowers of plants of the new *Impatiens* are red and light reddish pink bi-colored whereas flowers of plants of 'Tamar Purple Bicolor' are red purple in color with a darker central band.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (FIG. 1) is a side perspective view of a typical flowering plant of 'Dongipetresta 21' grown in a container.

Figure 2:
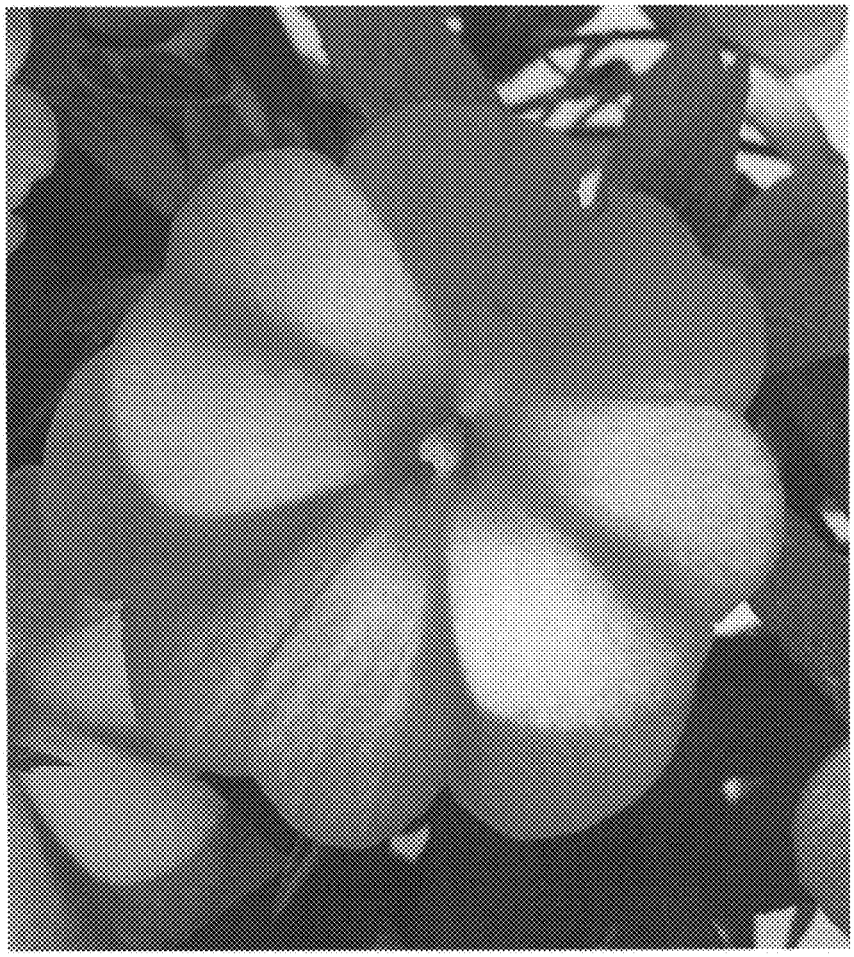

The photograph on the second sheet (FIG. 2) is a close-up view of a typical flower of 'Dongipetresta 21'.

DETAILED BOTANICAL DESCRIPTION

The aforementioned photographs and following observations, measurements and values describe plants grown during the summer and autumn in winter and early spring in 16.5-cm containers in a polyethylene-covered greenhouse in Encinitas, Calif. and under cultural practices typical of commercial New Guinea Impatiens production. During the production of the plants, day temperatures averaged 25° C., night temperatures averaged 18° C. and light levels ranged from 4,000 to 4,500 lux. Plants were 13 weeks old when the photographs were taken and 17 weeks old when the description was taken. In the following description, color references are made to The Royal Horticultural Society Colour Chart, 2015 Edition, except where general terms of ordinary dictionary significance are used.

Botanical classification: *Impatiens hawkeri* 'Dongipetresta 21'.

Parentage:

*Female, or seed, parent.*—*Impatiens hawkeri* 'Kiamuna', disclosed in U.S. Plant Pat. No. 20,983.

*Male, or pollen, parent.*—Proprietary selection of *Impatiens hawkeri* identified as code number NN12-003632-006, not patented.

Propagation:

*Type.*—By terminal vegetative cuttings.

*Time to initiate roots, summer and winter.*—About five to seven days at temperatures about 27° C. and night temperatures about 20° C.

*Time to produce a rooted young plant, summer and winter.*—About three weeks at day temperatures about 27° C. and night temperatures about 20° C.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Upright to outwardly spreading and mounding plant habit; broad inverted triangle in overall shape; freely branching habit with lateral branches potentially developing at every node; moderately vigorous to vigorous growth habit and moderate to rapid growth rate.

*Plant height.*—About 31 cm.

*Plant diameter.*—About 53 cm.

Lateral branch description:

*Length.*—About 24 cm.

*Diameter.*—About 1.25 cm.

*Internode length.*—About 6.25 cm.

*Strength.*—Strong, stout; flexible.

*Aspect.*—Initially upright to outwardly spreading.

*Texture and luster.*—Smooth, glabrous; glossy.

*Color, developing.*—Close to 187A.

*Color, fully developed.*—Close to 187A to 187B.

Leaf description:

*Arrangement.*—Typically in whorls; simple.

*Length.*—About 12.5 cm.

*Width.*—About 3.25 cm.

*Shape.*—Lanceolate to elliptic.

*Apex.*—Acuminate.

*Base.*—Cuneate.

*Margin.*—Senate with ciliation.

*Texture and luster, upper surface.*—Smooth, glabrous; glossy.

*Texture and luster, lower surface.*—Smooth, glabrous; semi-glossy.

*Venation pattern.*—Pinnate; arcuate.

*Color.*—Developing leaves, upper surface: Darker green than 147A. Developing leaves, lower surface: Close to 148A heavily overlain with close to 187B. Fully expanded leaves, upper surface: Darker green than N189A; midvein, close to 187B and lateral venation, darker green than N189A. Fully expanded leaves, lower surface: Close to 187A to 187B; venation, close to 187B.

*Petiole length.*—About 3.75 cm.

*Petiole diameter.*—About 3.5 mm.

*Petiole texture and luster, upper and lower surfaces.*—Smooth, glabrous; semi-glossy.

*Petiole color, upper and lower surfaces.*—Close to 187B.

Flower description:

*Flower type and flowering habit.*—Single, medium-sized rounded to slightly rectangular axillary flowers; freely flowering habit, typically about five to eight open flowers and flower buds per lateral branch; flowers positioned above and beyond the foliar plane, flowers typically face mostly upright to outwardly.

*Flower longevity.*—Flowers typically last about four to seven days on the plant under greenhouse conditions; petals self-cleaning, gynoecium persistent.

*Fragrance.*—None detected.

*Natural flowering season.*—Year-round under greenhouse conditions; in the garden, flowering from spring until fall in California; early flowering habit, plants typically begin flowering about ten weeks after planting.

*Flower buds.*—Length: About 1.2 cm. Diameter: About 8 mm. Shape: Ovoid. Texture and luster: Smooth, glabrous; glossy. Color: Petals, close to N45A; sepals, close to 187A to 187C.

*Flower diameter.*—About 5.9 cm by 6.2 cm.

*Flower depth.*—About 1.5 cm.

*Petals.*—Quantity and arrangement: Five per flower in a single whorl. Length, banner petal: About 2.8 cm. Length, lateral petals: About 2.8 cm. Length, lower petals: About 3.5 cm. Width, banner petal: About 3.5 cm. Width, lateral petals: About 2.9 cm. Width, lower petals: About 3.1 cm. Shape, banner petal: Broadly obcordate. Shape, lateral and lower petals: Cordate. Apex, all petals: Cordate. Base, all petals: Cuneate. Margin, all petals: Mostly entire with occasional and random indentations. Texture and luster, all petals, upper surface: Smooth, glabrous; velvety; slightly glossy; iridescent. Texture and luster, all petals, lower surface: Smooth, glabrous; slightly glossy; iridescent. Color, all petals: When opening and fully opened, upper surface: Centers, close to N45A; towards the margins, close to NN155D variably tinged with close to N45A; venation, similar to lamina color; color does not change with development. When opening and fully opened, lower surface: Close to between 45C and 46C; towards the margins, close to NN155D heavily overlain with close to between 45C and 46C; venation, close to NN78B and NN78C; color does not change with development.

*Sepals.*—Quantity and arrangement: Three in a single whorl; one modified into an elongated spur. Lateral sepal length: About 1 cm. Lateral sepal width: About 5 mm. Spur sepal length: About 1.5 cm. Spur sepal width: About 1.25 cm. Sepal shape: Elongated deltoid. Sepal apex: Cuspidate. Sepal base: Truncate. Sepal margin: Entire. Sepal texture and luster, upper surface: Smooth, glabrous; matte. Sepal texture and luster, lower surface: Smooth, glabrous; slightly glossy. Lateral sepal color, upper surface: Close to 157A to 157C. Lateral sepal color, lower surface: Close to 178A. Spur sepal color, upper and lower surfaces: Close to NN155D variably overlain with close to N57A. Spur length: About 3.5 cm. Spur diameter: At flower, about 2 5 mm; at apex, less than 1 mm. Spur texture and luster: Smooth, glabrous; semi-glossy. Spur color: Close to 54A to 54B; distally, close to 145A.

*Peduncles.*—Length: About 4.5 cm. Diameter: About 2 mm. Angle: About 30° to 45° from stein axis. Strength: Strong; flexible. Texture and luster: Smooth, glabrous; semi-glossy. Color: Close to 146B.

*Reproductive organs.*—Stamens: Quantity: Five fused at anthers; filaments free. Anther size: About 5 mm by 1.5 mm. Anther shape: Oblong. Anther color: Close to 8D; proximally, close to N57A. Pollen amount: Scarce to moderate. Pollen color: Close to 10D. Pistils: Quantity per flower: One. Pistil length: About 4 mm. Stigma shape: Crested. Stigma color: Close to 144A. Style color: Close to 144A. Ovary color: Close to 144A.

*Seeds and fruits.*—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Dongipetresta 21' as illustrated and described.

* * * * *